United States Patent
Chi et al.

(10) Patent No.: US 11,741,599 B2
(45) Date of Patent: Aug. 29, 2023

(54) METHOD FOR TREATING ARTERIAL STENOSIS

(71) Applicants: MacKay Memorial Hospital, Taipei (TW); National Chiao Tung University, Hsinchu (TW)

(72) Inventors: Shen Chi, Hsinchu County (TW); Po-Lin Lin, Hsinchu (TW); Ying-Hsiang Lee, Taipei (TW); Yu-Min Liu, Hsinchu (TW); Long Hsu, Hsinchu (TW); Ruo-Jing Ho, New Taipei (TW); Chang Francis Hsu, Hsinchu (TW); Han-Ping Huang, Yilan County (TW)

(73) Assignees: MacKay Memorial Hospital, Taipei (TW); National Chiao Tung University, Hsinchu (TW)

( * ) Notice: Subject to any disclaimer, the term of this patent is extended or adjusted under 35 U.S.C. 154(b) by 455 days.

(21) Appl. No.: 16/988,716

(22) Filed: Aug. 10, 2020

(65) Prior Publication Data
US 2022/0044393 A1    Feb. 10, 2022

(51) Int. Cl.
*G06T 7/00*      (2017.01)
*A61F 2/82*      (2013.01)
*G06F 17/18*     (2006.01)

(52) U.S. Cl.
CPC .............. *G06T 7/0012* (2013.01); *A61F 2/82* (2013.01); *G06F 17/18* (2013.01); *A61F 2002/823* (2013.01); *G06T 2207/30104* (2013.01)

(58) Field of Classification Search
CPC . G06T 2207/30104; G06T 2207/30101; G06T 2207/30172; A61B 6/504; A61B 6/5217
See application file for complete search history.

(56) References Cited

U.S. PATENT DOCUMENTS

2007/0216678 A1 * 9/2007 Rouet ................... G06T 7/0012
                                                      345/423
2018/0330507 A1 * 11/2018 Schormans ............ A61B 5/318

OTHER PUBLICATIONS

Maruhashi, Tatsuya, et al. "Diagnostic criteria of flow-mediated vasodilation for normal endothelial function and nitroglycerin-induced vasodilation for normal vascular smooth muscle function of the brachial artery." Journal of the American Heart Association 9.2 (Jan. 8, 2020) (Year: 2020).*

(Continued)

*Primary Examiner* — Vincent Rudolph
*Assistant Examiner* — Raphael Schwartz

(57) ABSTRACT

Disclosed herein is a method of treating a subject having arterial stenosis. The method comprises: (a) providing a plurality of image frames of an artery of the subject taken in sequence; (b) in a plurality of cross-sections of the artery, determining a maximum diameter and a minimum diameter of each of the plurality of cross-sections of the artery among the plurality of image frames of the step (a); (c) calculating an average vasodilation ratio of the artery base on the maximum diameter and the minimum diameter determined in the step (b); and (d) treating the subject based on the average vasodilation ratio calculated in the step (c), by implanting a stent to the subject when the average vasodilation ratio is equal to or greater than 0.2; or administering to the subject an effective amount of a vasodilator when the average vasodilation ratio is less than 0.2.

7 Claims, 2 Drawing Sheets

(56) References Cited

OTHER PUBLICATIONS

Schedel, Hannes, et al. "Primary stent placement for intrarenal aortic stenosis: immediate and midterm results." Journal of vascular and interventional radiology 15.4 (2004): 353-359. (Year: 2004).*
Touati, Julien, et al. "A robust construction algorithm of the centerline skeleton for complex aortic vascular structure using computational fluid dynamics." Computers in Biology and Medicine 86 (2017): 6-17. (Year: 2017).*
Massie, Barry M., et al. "Vasodilator treatment with isosorbide dinitrate and hydralazine in chronic heart failure." Heart 45.4 (1981): 376-384. (Year: 1981).*

* cited by examiner

METHOD FOR TREATING ARTERIAL STENOSIS

BACKGROUND OF THE INVENTION

1. Field of the Invention

The present disclosure in general relates to the field of treating arterial stenosis. More particularly, the present disclosure relates to a method for treating arterial stenosis based on the average vasodilation ratio determined by diameter differences of an artery.

2. Description of Related Art

Arterial stenosis is the narrowing of the exit of the left ventricle of the heart (where the aorta begins) and is known to be the leading cause of heart failure worldwide. The conventional practice for diagnosing arterial stenosis involves the assessment of the diseased vessel either visually or by Quantitative Coronary Angiography (QCA), which, however, both fail to provide a coronary functional assessment of the effect of the lesion on blood flow through the vessel. On the other hand, the fractional flow reserve (FFR) has been recognized as a reliable indicator for determining the degree of artery (e.g., coronary) occlusion, as the FFR is more effective in identifying ischemia causing lesions, as compared to the conventional invasive angiography. In practice, measuring the FFR by inserting a pressure wire into the stenosed vessel has been shown to be a better option for guiding revascularization decisions.

However, pressure wire based FFR measurements involve risks associated with the intervention necessary to insert the pressure wire into the vessel, and for a very narrow stenosis, the pressure wire may induce an additional pressure drop. In order to reduce the risk resulted from invasive procedures some mechanistic models are proposed, which use mathematical equations to model the physics of the blood flow in a three-dimensional anatomical model of the coronary vessels of a patient extracted from medical images. Such approaches rely on physics-based mathematical equations to model the physiology at rest and at hyperemia, thereby allowing one to numerically solve the equations on a computer and determine the flow and pressure drop for an individual patient.

However, a drawback of such mechanistic models is the high computational cost and complexity of associated with the model preparation and numerical solution of the physics-based equations. Additionally, such mechanistic models typically incorporate only anatomical and some partial physiological measurements and meanwhile omit other meaningful measurements. Even machine learning methods can be applied on the calculation of one or more hemodynamic indices, a large amount of computational cost still exists and therefore unsuitable for the time-limited clinical diagnosis.

In view of the foregoing, there exists in the related art a need for an improved method for determining arterial stenosis and treating a subject in need thereof.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, the present disclosure aims at providing a method for treating a subject having arterial stenosis mainly based on the diameter differences of the blood vessel by the non-invasive operation, and specifically providing a method that is characterized in not having the step of measuring blood flow in the blood vessel.

In one aspect, the disclosure is directed to a method of treating a subject having arterial stenosis. The method comprises: (a) providing a plurality of image frames of an artery of the subject taken in sequence; (b) in a plurality of cross-sections of the artery, determining a maximum diameter and a minimum diameter of each of the plurality of cross-sections of the artery among the plurality of image frames of the step (a); (c) calculating an average vasodilation ratio of the artery base on the maximum diameter and the minimum diameter of each the plurality of cross-sections of the artery determined in the step (b); and (d) treating the subject based on the average vasodilation ratio calculated in the step (c), by implanting a stent to the subject when the average vasodilation ratio is equal to or greater than 0.2.

According to embodiments of the present disclosure, the method is characterized in not having the step of measuring blood flow in the artery, and is further characterized in operating non-invasively without using any of a catheter, a sheath, a guidewire, or a combination thereof.

According to some embodiments of the present disclosure, in the step (b), the maximum diameter and the minimum diameter are determined by the steps of (i) determining a boundary and a central axis of the artery via aligning each of the plurality of image frames; (ii) selecting the plurality of cross-sections in the artery according to the normal vector of the central axis determined in the step (i); and (iii) determining the maximum diameter and the minimum diameter of each of the plurality of cross-sections selected in the step (ii) among the plurality of image frames based on the boundary determined in the step (i).

Preferably, in the above-mentioned step (i), the central axis of the artery is determined by performing a polynomial regression analysis on the aligned plurality of image frames.

According to some embodiments of the present disclosure, in the step (c), the average vasodilation ratio is calculated by using equations (1) and (2):

$$V_i = (D_{max,i} - D_{min,i})/D_{min,i}, \quad (1)$$

$$V_{avg} = \frac{\sum_{i=1}^{n} V_i}{n}, \quad (2)$$

wherein i represents any of the plurality of cross-sections of the artery, n represents the total number of the plurality of cross-sections, $D_{max,i}$ is the maximum diameter of the artery in the cross-section i, $D_{min,i}$ is the minimum diameter of the artery in the cross-section i, $V_i$ is a vasodilation ratio corresponding to the cross-section i, and $V_{avg}$ represents the average vasodilation ratio of the artery.

In some optional embodiments, the method further comprises administering to the subject an angiographic agent prior to the step (a), wherein the angiographic agent is adenosine, dipyridamole, isosorbide dinitrate, or a combination thereof.

According to certain embodiments of the present disclosure, in the step (a), the plurality of image frames are taken in a frame rate about 30 to 60 frames per second.

According to certain embodiments of the present disclosure, in the step (a), the plurality of image frames are taken in a period of about 5 to 8 seconds.

By virtue of the above technical feature, the method of the present disclosure can precisely determine which type of treatment to administer to a given subject in need.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
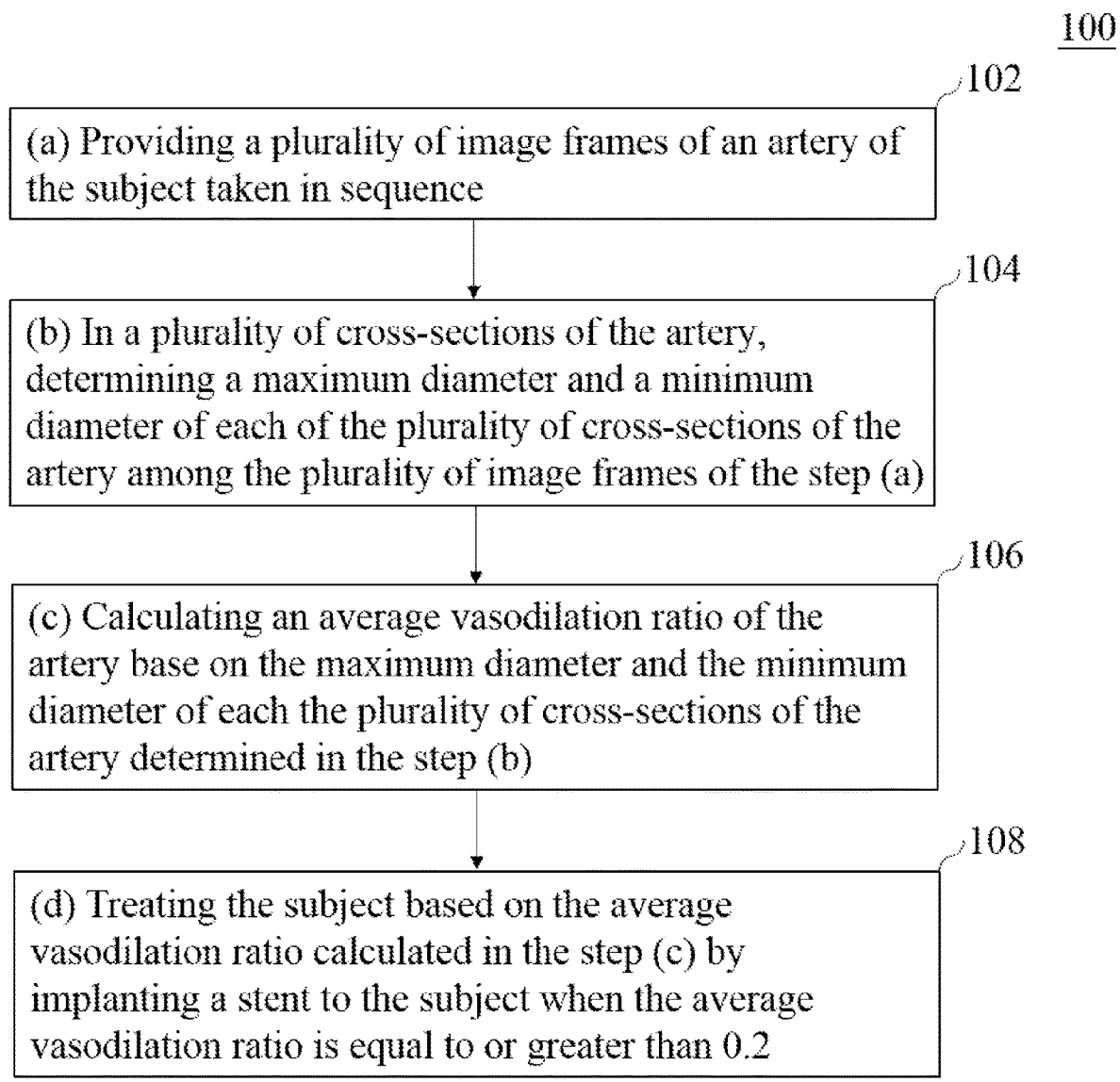
FIG. 1 is a flow chart illustrating a present method 100 for treating a subject having arterial stenosis according to the embodiment of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "image frame(s)" or "frame(s)" as used herein refers to one or more still images which compose the complete moving picture taken by photo capturing devices and/or software. Generally, the single images can be recorded on a strip of photographic film or as digital files with a time sequence, and can be integrated to collectively present a continuously moving action. The frames in the present invention can be taken by any medical imaging device such as X-ray radiography, magnetic resonance imaging, medical ultrasonography, endoscopy, elastography, tactile imaging, thermography, positron emission tomography (PET) and single-photon emission computed tomography. The term "sequence of frame" or "framing sequence" as used herein refers to a series of pictures taken in a given time, and the frequency that each frame is taken is called "frame rate" or "frame frequency", which is often expressed in hertz.

The term "image registration" or "image alignment" as used herein refers to the process of transforming different sets of data (e.g., multiple photographs or images, view points, or times) into one coordinate system. In the present application, "image registration" or "image alignment" is applied on multiple medical images. Specifically, the practical idea of the algorithms for performing image registration or image alignment is to respectively designate one of the images as a target image and the others as the source/moving image(s), and the "image registration" or "image alignment" involves spatially transforming the source/moving image(s) to align with the target image.

The term "vasodilation" as used herein refers to the widening of blood vessels that results from relaxation of smooth muscle cells within the vessel walls, in particular in the arteries, e.g., aorta, coronary arteries and large arteries. A "vasodilation ratio" is used to represent a degree of vessel widening, which is often affected by vascular occlusion. In the present invention, the "vasodilation ratio" is determined by the differences between a maximum diameter and a minimum diameter of a given cross-section in a certain segment of the artery without measuring the blood flow therein.

As used herein, the term "treat," "treating" and "treatment" are interchangeable, and encompasses partially or completely preventing, ameliorating, mitigating and/or managing a symptom, a secondary disorder or a condition associated with arterial stenosis, in which dilating the vessels and/or reducing vascular occlusion provide a benefit to the subject having or suspected of having such symptom, disorder or condition. The term "treating" as used herein refers to application or administration of one or more medicaments and medical equipment based on the threshold determined by the method of the present disclosure to a subject, who has a symptom, a secondary disorder or a condition associated with arterial stenosis, with the purpose to partially or completely alleviate, ameliorate, relieve, delay onset of, inhibit progression of, reduce severity of, and/or reduce incidence of one or more symptoms, secondary disorders or features associated with arterial stenosis. Symptoms, secondary disorders, and/or conditions associated with arterial stenosis include, but are not limited to, breathlessness, chest pain (angina), pressure or tightness, syncope, palpitations, noticeable heartbeats, declining in activity level and heart murmur. Treatment is administered to a subject who exhibits a certain developing degree of such symptoms, disorder, and/or condition for the purpose of decreasing the risk of developing the symptoms, secondary disorders, and/or conditions associated with arterial stenosis based on the determined vasodilation ratio calculated by the present method. Treatment is generally "effective" if one or more symptoms are reduced or if the progression of a symptom, disorder or condition is halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/kg). Alternatively, the effective amount can be expressed in the concentration of the active component (e.g., the vasodilator), such as molar concentration, mass concentration, volume concentration, molality, mole fraction, mass fraction and mixing ratio. Specifically, the term "therapeutically effective amount" used in connection with the vasodilator described herein refers to the quantity of any one of vasodilator, which are sufficient to alleviate or ameliorate the symptoms associated with the arterial stenosis in the subject. Persons having ordinary skills could determine the dose for the vasodilator (such as, nitroglycerin or alprostadil) according to practical needs and medical knowledge.

The term "subject" refers to a mammal including the human species that is treatable with methods of the present invention. The term "subject" is intended to refer to both the male and female gender unless one gender is specifically indicated.

II. Description of the Invention

The present disclosure is directed to a treating method for a subject having arterial stenosis based on the determination by calculating the diameter differences of a given vessel.

Accordingly, the aspect of the present disclosure is directed to a method of treating a subject having or suspected of having arterial stenosis. Referring to FIG. 1, which is a flow chart depicting the steps of the present method 100. The present method 100 includes at least, the following steps, which are respectively indicated by reference numbers 102 to 108 in FIG. 1, (a) providing a plurality of image frames of an artery of the subject taken in sequence;

(b) in a given plurality of cross-sections of the artery, determining a maximum diameter and a minimum diameter of each of the plurality of cross-sections of the artery among the plurality of image frames of the step (a);

(c) calculating an average vasodilation ratio of the artery base on the maximum diameter and the minimum diameter determined in the step (b); and (d) treating the subject based on the average vasodilation ratio calculated in the step (c), by implanting a stent to the subject when the average vasodilation ratio is equal to or greater than 0.2; or administering to the subject an effective amount of a vasodilator when the average vasodilation ratio is less than 0.2.

Before starting the present method 100, a selected segment of an artery of a human, usually the most occlusive segment, is chosen for taking medical images. In some embodiments, the selected vessel preferably is the left anterior descending branch of the coronary artery. Then, X-ray radiography is performed to capture the image of the selected segment of the artery, which is injected with an X-ray contrast agent prior to X-ray radiography. The choice of the X-ray contrast agent and the injected dosage may vary with the need of each subject, as long as the images thus generated are readable by those skilled in the art.

Alternatively, or optionally, an angiographic agent can be administered to the subject before taking the medical images, so as to temporarily clear the blockage of the selected vessel and instantly increases the blood flow therein. Examples of the commonly used angiographic agent include, but are not limited to, adenosine, dipyridamole, isosorbide dinitrate, and a combination thereof.

In the step (a), the medical images of a given segment of the artery are continuously taken in a predetermined period of time. In one embodiment, the X-ray images of a specific vascular section are continuously taken in a period of about 5 to 8 seconds at a frequency about 30 to 60 frames per second, such as 30, 32, 35, 37, 40, 42, 45, 47, 50, 52, 55, 56, 57, 58, 59 or 60 frames per second. In a preferred embodiment, the plurality of image frames are taken in a period of 6 seconds at a frame rate of 45 hertz (Hz).

Next, in the step (b), a maximum diameter and a minimum diameter of the artery in a specified cross-section among the plurality of image frames taken in the step (a) are determined. Preferably, a plurality of cross-sections among the plurality of image frames taken in the step (a) may be specified, and the maximum and minimum diameters of the artery in each cross-section are determined. Specifically, in the step (b), image registration is performed on the plurality of image frames taken in the step (a), that is, each of the plurality of image frames are aligned, and subjected to a frame analysis to determine the boundary and the central axis of the artery in each image frame. Specifically, the frame alignment can be executed by conventional algorithms, such as eigenvalue algorithms, to determine the region and the area of the arterial segment to be read. In one example, Kanade-Lucas-Tomasi (KLT) algorithm is performed, by which the aligned image frames are anchored, then Tracking algorithms are applied to track multiple point features in each frame pictures and to zoom and/or rotate the frame pictures, such that each of the plurality of image frames are combined in accordance with the common point features. In some cases, the final image frame in the frame series is designated as a standard template with a fixed relative position, so as to facilitate the alignment and anchor of the rest of the image frames. After anchoring and combining the image frames, the plurality of images frames are subjected to a binarization process to simplify the target object and minimize the background information, such that the boundary of the arterial vessel is determined. Then, a polynomial regression analysis is performed to determine the central axis based on the determined boundary.

Still referring to the step (b), once the central axis and the boundary of the selected artery in the pictures are determined, then the diameter of the artery can be determined. Specifically, at least one sampling points are assigned on the central axis. Accordingly, at least one cross-section can be determined within the selected arterial segment in the picture via the normal vector of each sampling point on the central axis. Specifically, one sampling point on the central axis forms a corresponding cross-section of the artery, and in each of the plurality of image frames, the diameter of the artery between two boundaries in that cross-section can be obtained. It should be noted that the number of sampling points or the cross-sections varies according to practical needs. In a working example, a plurality of sampling points are selected in the aligned image frames, for example, the number of sampling points is preferably 20-500, such as 20, 30, 40, 50, 100, 200, 300, 400 or 500. In certain example, the number of sampling points is more preferably 200. The diameter in any selected cross-section of the artery changes with time due to the pulse and blood flow, and is reflected on the plurality of image frames taken continuously in that period. Hence, a maximum diameter and a minimum diameter for each sampling point may be determined by sorting the plurality of image frames collected herein.

Next, in the step (c), based on the determined maximum and minimum diameters in the step (b), an average vasodilation ratio of the artery is calculated. Preferably, the average vasodilation ratio is calculated by using equations (1) and (2):

$$V_i = (D_{max,i} - D_{min,i})/D_{min,i}, \quad (1)$$

$$V_{avg} = \frac{\sum_{i=1}^{n} V_i}{n}. \quad (2)$$

In the equations (1) and (2), i represents any given cross-section of the plurality of cross-sections of the artery, n represents a total number of the plurality of cross-sections (i.e., the sampling points, correspondingly), $D_{max,i}$ is the maximum diameter of the artery in the given cross-section i, $D_{min,i}$ is the minimum diameter of the artery in the given cross-section i, $V_i$ is a vasodilation ratio of the artery corresponding to the given cross-section i, and $V_{avg}$ represents the average vasodilation ratio of the artery.

In some embodiments, the $V_g$ has a negative correlation to a hemodynamics parameter. The hemodynamics parameter may be an indicator of blood flow, such as coronary flow reserve (CFR) and fractional flow reserve (FFR). In some embodiments, the hemodynamics parameter is FFR, which is defined as the ratio of the maximal blood flow in the stenotic vessel to the maximal blood flow in a normal vessel, and may be an indicium of the severity of stenosis. In one preferred example, the average vasodilation ratio has a negative correlation with FFR, preferably, the average vasodilation ratio is negatively correlated with FFR via a coefficient of about −0.9 to −0.95. In one preferred example, the average vasodilation ratio and FFR meet the function as defined in equation (3):

$$V_{avg} = -1.13 FFR + 1.1954 \quad (3).$$

According to the present disclosure, since FFR is a well-recognized blood occlusion indicator, average vasodilation ratio, which correlates with FFR may also serve as a blood occlusion indicator. Hence, in the working example, the degree of vascular occlusion may be obtained by calculating the average vasodilation ratio that reflect the degree of vascular occlusion as required by the equation (3).

It should be noted that, within the present method 100, the steps for estimating the level of occlusion in vessels of the present disclosure do not involve any step directed to the measurement of the blood flow in the artery. More specifically, the present disclosure only utilizes the differences in the vessels' diameters as indicia for determining the degree of artery occlusion. By determining the differences between vessel diameters within a limited period of time, an appropriate treatment for the subject or patient can be applied thereto.

In addition, the present steps (a) to (c), or steps for estimating the level of occlusion in vessels, they are executed non-invasively, specifically, without using of any catheter, sheath, guidewire, or a combination thereof, conventionally required for facilitating the detection.

Next, in the step (d), an appropriate treatment is administered to the subject based on the average vasodilation ratio obtained in the steps (a)-(c). The treatment can be a surgery (e.g., a stent implantation and/or coronary bypass surgery), an effective amount of a vasodilator (e.g., nitroglycerin, alprostadil, and/or riociguat), or a combination thereof.

According to some embodiments of the present disclosure, the treatment is a stent implantation, which may increase the blood flow into the occlusive arteries of the subject, and may be performed one or more times. Alternatively, the treatment is a coronary bypass surgery that restores normal blood flow to the occlusive coronary artery. Each surgery can be independently performed by a time period of one month, two months, three months, four months, six months, nine months, one year, two years, three years, four years, five years, seven years, ten years, fifteen years, and twenty years of the lifetime of the subject. In certain embodiments, the first implantation and a subsequent implantation are performed in the period of six months apart. In certain embodiments, the first surgery and its subsequent surgery are performed in the period of three years apart. In certain embodiments, the first and second implantation surgeries are performed in a period of ten years apart.

In one preferred example, a stent is implanted to the subject when the average vasodilation ratio is equal to or greater than 0.2.

According to other embodiments of the present disclosure, the treatment is administering an effective amount of a vasodilator to the subject, in which the vasodilator may dilates blood vessels and allows more blood to flow through. Examples of the vasodilator include, but are not limited to, nitroglycerin, alprostadil, riociguat, hydralazine, minoxidil, nesiritide, nitroprusside and etc.

The amount of the vasodilator required to achieve an effective treatment will vary from subject to subject, depending, for example, on age and general condition of a subject, severity of the side effects or disorder, mode of administration, and the like. An effective amount may be included in a single dose (e.g., single oral dose) or multiple doses (e.g., multiple oral doses). In certain embodiments, when multiple doses are administered to a subject, any two doses of the multiple doses may include different or substantially the same amounts of the vasodilator described herein. In certain embodiments, the vasodilator is administered to the subject at the frequency of three doses a day, two doses a day, one dose a day, one dose every other day, one dose every third day, one dose every week, one dose every other week, one dose monthly, one dose every other month, and etc. In certain embodiments, the vasodilator is administered to the subject at the frequency of one dose per day. In certain embodiments, the vasodilator is administered to the subject at the frequency of two doses per day. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, of a vasodilator described herein.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

1. Establishing the Average Vasodilation Ratio Model

Twenty-five patients having confirmed diagnosis of arterial stenosis were randomly selected from the medical database of MacKay Memorial Hospital (Taiwan), in which a clinically measured FFR value for each patient is stored.

A segment of the left anterior descending arteries of each patient was selected and injected with 1 mg of isosorbide dinitrate, immediately followed by continuously taking the X-ray medical images in a period of 8 seconds. The frame rate was 45 hertz (i.e., 45 frames in one second), and the final frame was assigned as a template frame. After region of interest (ROI) of the image was selected, each of the image frames were subjected to Kanade-Lucas-Tomasi (KLT) algorithm, Tracking algorithm and image processing (e.g., zooming and rotating each frame), allowing the common point features among all the image frames being anchored, and all the image frames were aligned via the anchored point features. The thus-aligned image frames were subsequently subjected to a binarization process and a polynomial regression analysis, by which the boundary and the central axis of the artery were determined.

The diameter corresponding to 200 sampling points on the central axis along the arterial vessels in each image frame were calculated by using the normal vector of each sampling point.

The average vasodilation ratio of each individual was calculated via the following equations:

$$V_i = (D_{max,i} - D_{min,i})/D_{min,i}, \quad (1)$$

$$V_{avg} = \frac{\sum_{i=1}^{n} V_i}{n}, \quad (2)$$

wherein i represents any of the XX cross-sections of the artery, n represents the total number of the plurality of cross-sections (i.e., the XX sampling points, correspondingly), $D_{max,i}$ is the maximum diameter of the artery in the cross-section i, $D_{min,i}$ is the minimum diameter of the artery in the cross-section i, $V_i$ is a vasodilation ratio corresponding to the cross-section i, and $V_{avg}$ represents the average vasodilation ratio of the artery.

2. Correlation Between the Average Vasodilation Ratio Model and FFR

Figure 2:
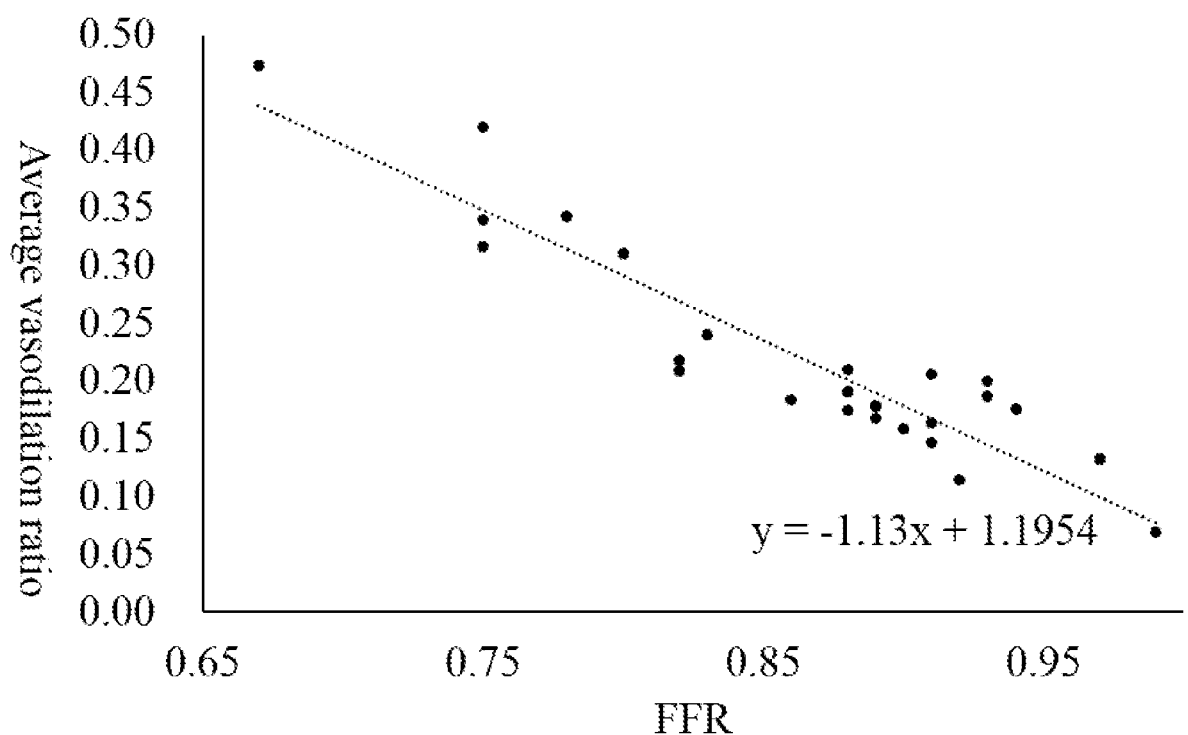
FIG. 2 depicts the line of regression of the average vasodilation ratio on FFR according to one working example of the present disclosure.

The average statistical results of average vasodilation ratio of 25 patients are depicted in FIG. 2, in which the average vasodilation ratio and the FFR value for each patient satisfied the following equation: $V_{avg}=-1.13$ FFR+1.1954, and the correlation coefficient was about −0.92.

3. Clinical Diagnosis for Arterial Stenosis Via the Average Vasodilation Ratio Model of Example 1

Clinically, when the average vasodilation ratio of any given patient is less than 0.2, it means less likely of significant and actual coronary stenosis, thus treating underlying diseases (such as obesity, hypertension, etc.) with optimal antianginal medication and/or vasodilator is favored. On the contrary, when the average vasodilation ratio of one patient is equal to or above than 0.2, further stent implantation for increase coronary flow is favored.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a subject having arterial stenosis, comprising,
(a) providing a plurality of image frames of an artery of the subject taken in sequence;
(b) in a plurality of cross-sections of the artery, determining a maximum diameter and a minimum diameter of each of the plurality of cross-sections of the artery among the plurality of image frames of the step (a);
(c) calculating an average vasodilation ratio of the artery based on the maximum diameter and the minimum diameter of each of the plurality of cross-sections of the artery determined in the step (b) by using equations (1) and (2):

$$V_i = (D_{max,i} - D_{min,i})/D_{min,i}, \quad (1)$$

$$V_{avg} = \frac{\sum_{i=1}^{n} V_i}{n}, \quad (2)$$

wherein i represents any of the plurality of cross-sections of the artery, n represents the total number of the plurality of cross-sections, $D_{max,i}$ is the maximum diameter of the artery in the cross-section i, $D_{min,i}$ is the minimum diameter of the artery in the cross-section i, $V_i$ is a vasodilation ratio corresponding to the cross-section i, and $V_{avg}$ represents the average vasodilation ratio of the artery; and (d) treating the subject based on the average vasodilation ratio calculated in the step (c) by implanting a stent to the subject when the average vasodilation ratio is equal to or greater than 0.2; and wherein the method is characterized in not having a step of measuring blood flow in the artery.

2. The method of claim 1, wherein in the step (b), the maximum diameter and the minimum diameter are determined by the steps of,
  (i) determining a boundary and a central axis of the artery via aligning each of the plurality of image frames;
  (ii) selecting the plurality of cross-sections in the artery according to the normal vector of the central axis determined in the step (i); and
  (iii) determining the maximum diameter and the minimum diameter of each of the plurality of cross-sections selected in the step (ii) among the plurality of image frames based on the boundary determined in the step (i).

3. The method of claim 2, wherein in the step (i), the central axis of the artery is determined by performing a polynomial regression analysis on the aligned plurality of image frames.

4. The method of claim 1, further comprising administering to the subject an angiographic agent prior to the step (a), wherein the angiographic agent is adenosine, dipyridamole, isosorbide dinitrate or a combination thereof.

5. The method of claim 1, wherein in the step (a), the plurality of image frames are taken in a frame rate about 30 to 60 frames per second.

6. The method of claim 1, wherein in the step (a), the plurality of image frames are taken in a period of about 5 to 8 seconds.

7. The method of claim 1, wherein the steps (a) to (c) of the method are characterized in operating non-invasively without using any of a catheter, a sheath, a guidewire, or a combination thereof.

* * * * *